United States Patent [19]

Large

[11] 4,376,644

[45] * Mar. 15, 1983

[54] TRI-MIXED ALKYLSULFONIUM SALTS OF N-PHOSPHONOMETHYLGLYCINE AND THEIR USE AS PLANT GROWTH REGULATORS AND HERBICIDES

[75] Inventor: George B. Large, Orinda, Calif.

[73] Assignee: Stauffer Chemical Company, Westport, Conn.

[ * ] Notice: The portion of the term of this patent subsequent to Feb. 16, 1999, has been disclaimed.

[21] Appl. No.: 324,284

[22] Filed: Nov. 25, 1981

Related U.S. Application Data

[63] Continuation-in-part of Ser. No. 212,921, Dec. 4, 1980, Pat. No. 4,315,765.

[51] Int. Cl.$^3$ .................. C07F 9/38; A01N 57/00
[52] U.S. Cl. .................. 71/87; 260/502.5 F
[58] Field of Search .................. 260/502.5; 71/87

[56] References Cited

U.S. PATENT DOCUMENTS

| | | | |
|---|---|---|---|
| 2,854,791 | 10/1958 | Antognini | 47/58 |
| 3,101,265 | 8/1963 | Smuthy et al. | 71/2.7 |
| 3,235,356 | 2/1966 | Herschler | 71/2.3 |
| 3,652,255 | 3/1972 | Osieka et al. | 71/76 |
| 3,799,758 | 3/1974 | Franz | 71/86 |
| 3,835,000 | | Frazier et al. | 204/78 |
| 3,853,530 | 12/1974 | Franz | 71/76 |
| 3,929,450 | 12/1975 | Hamm et al. | 71/86 |
| 3,977,860 | 8/1976 | Franz | 71/86 |
| 3,988,142 | 10/1976 | Franz | 71/86 |
| 4,059,431 | 11/1977 | Takematsu et al. | 71/87 |
| 4,059,432 | 11/1977 | Takematsu et al. | 71/87 |
| 4,147,719 | 4/1979 | Franz | 260/501.12 |
| 4,251,259 | 2/1981 | Preziuso et al. | 71/88 |
| 4,341,549 | 7/1982 | Large et al. | 260/502.5 |

Primary Examiner—Joseph E. Evans
Attorney, Agent, or Firm—Harry A. Pacini

[57] ABSTRACT

Novel tri-mixed alkylsulfonium salts of N-phosphonomethylglycine are disclosed herein, having the formula

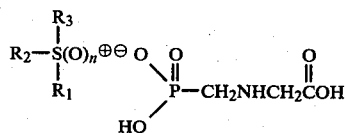

in which $R_1$, $R_2$, and $R_3$ represent $C_1$-$C_6$ alkyl and n is zero or one, wherein no more than two of $R_1$, $R_2$, or $R_3$ are identical. The compounds are useful in regulating the natural growth or development of plants and as herbicides.

33 Claims, No Drawings

TRI-MIXED ALKYLSULFONIUM SALTS OF N-PHOSPHONOMETHYLGLYCINE AND THEIR USE AS PLANT GROWTH REGULATORS AND HERBICIDES

CROSS REFERENCE TO RELATED APPLICATION

This is a continuation-in-part of application Ser. No. 212,921, filed Dec. 4, 1980, now U.S. Pat. No. 4,315,765.

BACKGROUND OF THE INVENTION

This invention is directed to novel chemical compounds and their use in regulating the natural growth or development of plants. In particular, this invention relates to the chemical treatment of plants to alter their natural growth or development for the purpose of enhancing various agricultural or horticultural features of the plants, and also to the control of undesirable vegetation.

It is well known among those skilled in the art of agriculture and horticulture that various features of plant growth can be modified or regulated to produce a variety of beneficial effects.

For instance, certain types of treatment can produce defoliation of a plant in a beneficial manner, i.e., inhibiting further leaf growth while permitting further development of the productive plant parts. As a result, the productive parts demonstrate extra growth, and subsequent harvesting operations are facilitated. Defoliants are particularly useful in flax, cotton, and bean crops, and other crops of a similar nature. Although defoliation results in the killing of leaves, it is not a herbicidal action per se since the remainder of the plant is unharmed. Indeed, killing of the treated plant is undesirable when defoliation is sought, since leaves will continue to adhere to a dead plant.

Another response demonstrated by plant growth regulants is the general retardation of vegetative growth. This response has a wide variety of beneficial features. In certain plants it causes a diminution or elimination of the normal apical dominance, and thus leads to a shorter main stem and increased lateral branching. This alteration of the natural growth or development produces smaller, bushier plants which often demonstrate increased resistance to drought and pest infestation. The retardation of vegetative growth in turf grasses is particularly desirable. When the vertical growth rate of such grasses is lessened, root development is enhanced and a denser, sturdier turf is produced. The retardation of turf grasses also serves to increase the interval between mowings of lawns, golf courses and similar grassy areas.

In many types of plants, such as silage crops, potatoes, sugar cane, beets, grapes, melons and fruit trees, the retardation of vegetative growth results in an increase in the carbohydrate content of the plants at harvest. It is believed that the retardation or suppression of such growth at the appropriate stage of development causes less of the available carbohydrate to be consumed for vegetative growth and results in an enhanced starch and/or sucrose content. Retardation of vegetative growth in fruit trees is demonstrated by shorter branches and greater fullness of shape, and often results in lesser vertical elongation. These factors contribute to the ease of access to the orchard and simplify the fruit harvesting procedure.

BRIEF DESCRIPTION OF THE INVENTION

It has now been discovered that novel tri-mixed alkylsulfonium salts of N-phosphonomethylglycine are useful in both regulating the natural growth or development of plants and in controlling undesirable vegetation. These salts have the formula

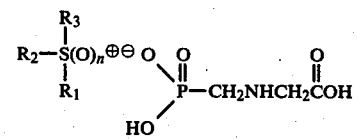

where $R_1$, $R_2$, and $R_3$ represent $C_1-C_6$ alkyl, and n is zero or one, wherein no more than two of $R_1$, $R_2$ or $R_3$ are identical. Preferably, $R_1$, $R_2$, and $R_3$ each represent $C_1-C_4$ alkyl, wherein no more than two of $R_1$, $R_2$ or $R_3$ are identical.

This invention further relates to a method of regulating the natural growth or development of plants comprising applying to said plants an effective, plant-regulating, non-lethal amount of the above compounds, as well as a method of controlling undesirable vegetation comprising applying a herbicidally effective amount of the compounds to such vegetation when the latter is in a postemergence state.

As employed herein, the term "natural growth or development" designates the normal life cycle of a plant in accordance with its genetics and environment, in the absence of artificial external influences. A preferred utility of the instant compounds is in increasing the source yield of field grown sugarcane and sorghum. The term "regulating" is used herein to denote the bringing about through chemical means of any temporary or permanent modification or variation from the normal life cycle short of killing the plant.

The term "herbicidally effective amount" designates any amount of the compounds disclosed herein which will kill a plant or any portion thereof. By "plants" is meant germinant seeds, emerging seedlings, and established vegetation, including roots and above-ground portions. Herbicidal effects include killing, defoliation, desiccation, stunting, leaf burn, and dwarfing. Herbicidal effects are generally achieved at higher application rates than growth regulating effects.

The term "alkyl" is used herein to include both straight-chain and branched-chain alkyl groups. The carbon atom range is intended to be inclusive of its upper and lower limits; for example, methyl, ethyl, n-propyl, isopropyl, butyl, n-butyl, sec.-butyl, pentyl, isopentyl, neopentyl, sec.-pentyl, hexyl, isohexyl, sec.-hexyl, and the like. Hence, the term "tri-mixed alkyl" represents alkyl substitutions in which the sulfonium cation contains three alkyl moieties. However, no more than two of said alkyl moieties are identical.

Examples of specific compounds falling within the above formula are:

diethylmethyl sulfonium salt of N-phosphonomethylglycine dimethylethyl sulfonium salt of N-phosphomethylglycine diethylisopropyl sulfonium salt of N-phosphonomethylglycine diethyl-n-butyl sulfonium salt of N-phosphonomethylglycine di-n-butylmethyl sulfonium salt of N-phosphomethylglycine dimethyl-n-butyl sulfonium salt of N-phosphonomethylglycine dimethylisopropyl sulfonium salt of N-phosphonomethylglycine

DETAILED DESCRIPTION OF THE INVENTION

In accordance with the instant invention, regulation of the natural growth or development of plants is achieved by the direct application of a compound within the above formula or a formulation of such a compound to the plants or to any of their above-ground portions at approximately 4 to 10 weeks prior to harvest. With properly controlled application, a growth regulating effect can be achieved without herbicidal results. The amount which constitutes an effective amount varies not only with the particular material selected for treatment, but also with the regulatory effect to be achieved, the species of plant being treated and its stage of development, and whether a permanent or transient effect is sought. Other factors which bear upon the determination of an appropriate plant regulating amount include the manner of application and weather conditions such as temperature or rainfall. Growth regulation may arise from the effect of the compound on either the physiological processes or the morphology of the plant, or from both in combination or in sequence. Morphological changes are generally noticeable by observable changes in the size, shape, color or texture of the treated plant or any of its parts, as well as in the quantity of fruit or flowers produced.

Changes in physiological processes, on the other hand, occur within the treated plant and are usually hidden from the eye of an observer. Changes of this type most often occur in the production, location, storage or use of chemicals naturally occurring in the plant, such as hormones. Physiological changes may be visually detectable when followed by a change in morphology. In addition, numerous analytical procedures for determining the nature and magnitude of changes in the various physiological processes are known to those skilled in the art.

The compounds of the instant invention serve to regulate the natural growth or development of treated plants in a number of diverse ways, and it is to be understood that each compound may not produce identical regulatory effects on each plant species or at every rate of application. As stated above, responses will vary in accordance with the compound, the rate, the plant, etc.

Herbicidal effects are achieved in a similar manner, and the strength of the application can be varied to achieve the desired result.

The compounds of this invention are readily prepared from N-phosphonomethylglycine by reacting the latter with silver oxide to form the silver salt or with sodium hydroxide to form the sodium salt, and treating either the silver or sodium salt with a trialkylsulfonium or -sulfoxonium halide. Alternatively, the glycine can be reacted directly with the trialkylsulfonium or -sulfoxonium halide in the presence of propylene oxide. N-Phosphonomethylglycine is a commercially available material known by the common name "glyphosate." It can be prepared by the phosphonomethylation of glycine, the reaction of ethyl glycinate with formaldehyde and diethylphosphite, or the oxidation of the N-phosphinomethylglycine. Such methods are described in U.S. Pat. No. 3,799,758 (Franz, Mar. 26, 1974).

As illustrated in the examples which follow, the compounds of the invention can either regulate the natural growth or development of plants or kill weeds. While regulatory responses are often desirable in their own right, their effect on crop economics is most often of primary significance. Thus, increases in the yield of individual plants, increases in the yield per unit area, and reductions in the cost of harvesting and/or subsequent processing are all to be considered in assessing the consequence of an individual regulatory effect during the growth or development of a plant.

The specific examples which follow are presented as merely illustrative, non-limiting demonstrations of the preparation of the compounds of the instant invention and of their effectiveness in regulating the growth of plants and in controlling undesirable vegetation.

EXAMPLE I

Di-n-butylmethyl sulfonium Salt of N-phosphonomethylglycine

A reaction vessel was charged with 50 milliliters (ml) of water, 5.1 grams (g) (0.03 mole) of N-phosphonomethylglycine, and 8.65 g (0.03 mole) of di-n-butylmethyl sulfonium iodide. The vessel was additionally charged with 2.2 g (0.0375 mole) of propylene oxide. The entire reaction mixture was allowed to stand at room temperature overnight. At the end of this time, the reaction mixture was extracted three times with diethyl ether and phase separated. The aqueous phase was stripped, yielding 11.1 g. This product was triturated with tetrahydrofuran (2×10 ml), then once with 10 ml acetone and stripped to yield 11.0 g of product. This product was further triturated with 20 ml of acetone and then with 10 ml diethyl ether and stripped. There was obtained a low melting solid, yield 9.8 g. The molecular structure of the product was confirmed by proton-nuclear magnetic resonance as the title compound.

EXAMPLE II

Diethylmethyl sulfonium Salt of N-phosphonomethylglycine

In a similar procedure as Example I, 50 ml of water, 6.76 g (0.04 mole) of N-phosphonomethylglycine, 9.3 g (0.04 mole) of diethylmethyl sulfonium iodide and 2.9 g (0.05 mole) of propylene oxide were reacted overnight at room temperature, extracted 3 times with diethyl ether and the aqueous phase stripped of volatile (yield 12.3 g). After trituration with acetone and diethyl ether and stripping of volatiles, there was obtained 12.0 g of the title compound (decomposes at 60°–65° C.). The molecular structure of the product was confirmed by proton-nuclear magnetic resonance as that of the title compound.

EXAMPLE III

Dimethylisopropyl sulfonium Salt of N-phosphonomethylglycine

In a similar procedure as Example I, 50 ml of water, 6.76 g (0.04 mole) of N-phosphonomethylglycine, 9.3 g (0.04 mole) of dimethylisopropyl sulfonium iodide and 3.5 g (0.06 mole) of propylene oxide were reacted overnight at room temperature, extracted 2 times with diethyl ether and the aqueous phase stripped (yield 11.8 g). After trituration with acetone (2 times, 10 ml each)

the product was stripped again to yield 11.2 g, $n_D^{30}$ 1.5232. The molecular structure of the product was confirmed by proton nuclear magnetic resonsance as that of the title compound.

EXAMPLE IV

Dimethyl-n-butyl sulfonium Salt of N-phosphonomethylglycine

In a similar procedure as Example I, 50 ml of water, 6.8 g (0.04 mole) of N-phosphonomethylglycine, 10.0 g (0.04 mole) of dimethyl-n-butyl sulfonium iodide and 3.5 g (0.06 mole) of propylene oxide were reacted overnight at room temperature, extracted 2 times with diethyl ether, phase separated, and stripped of volatiles (yield 12.4 g). After trituration with acetone (2 times, 10 ml each) and stripping, there was obtained 12.9 g of a hygroscopic white solid. The molecular structure of the product was confirmed by proton-nuclear magnetic resonance as the title compound.

Other compounds within the scope of the generic formula shown above can be prepared by either of these methods with appropriate starting materials.

This example demonstrates the post-emergence herbicidal activity of the compounds prepared in Examples I and II.

Aluminum planting flats measuring 15.2×22.9×8.9 cm were filled to a depth of 7.6 cm with loamy sand soil, containing 50 parts per million (ppm) each of the commercial fungicide cis-N[(trichloromethyl)thio]-4-cyclohexene-1,2-dicarboximide (Captan®) and 17—1—7—17 fertilizer (percentages of N—$P_2O_5$—$K_2O$) on a weight basis). Several rows were impressed across the width of each flat and a variety of seeds of both grass and broadleaf weed species were planted, one species per row. The weed species used are listed below:

| Grasses: | |
|---|---|
| A. Yellow nutsedge | Cyperus esculentus |
| B. Foxtail | Setaria sp. |
| C. Watergrass | Echinochloa crusgalli |
| D. Wild oat | Avena fatua |
| Broadleaf weeds: | |
| E. Curly dock | Rumex crispus |
| F. Annual morning glory | Ipomoea purpurea |
| G. Velvetleaf | Abutilon theophrasti |
| H. Mustard | Brassica sp. |

The broad leaf species were seeded first, and the grasses were seeded four days later. Ample seeds of each species were planted to produce 20 to 50 seedlings per row after emergence, depending on the size of each plant.

Ten days after the grasses were seeded, the emerged seedlings of all species were sprayed with aqueous solutions of the test compounds. The solutions were prepared to such dilutions that a spray rate of 80 gallons per acre (750 liters per hectare) gave 4.0 pounds of test compound per acre (4.48 kilograms per hectare) as desired for the test. Additional control flats not treated at all were used as standards for comparison to measure the extent of weed control in the treated flats.

Nineteen days later, the test flats were compared to the standards and the weeds in each row were rated visually in terms of percent control ranging from 0% to 100%, with 0% representing the same degree of growth as the same row in the standard and 100% representing complete kill of all weeds in the row. All types of plant injury were taken into consideration. The results are shown in Table I.

TABLE I

HERBICIDAL TEST RESULTS

| | | Percent Control | | | | | | | |
|---|---|---|---|---|---|---|---|---|---|
| | Application | Grass Weeds | | | | Broadleaf Weeds | | | |
| Test Compound | Rate (lb/A) | A | B | C | D | E | F | G | H |
| N—phosphonomethyl-glycine, di-n-butyl methyl sulfonium salt | 4.0 | 70 | 100 | 90 | 90 | 80 | 50 | 80 | 75 |
| N—phosphonomethyl-glycine, diethylmethyl sulfonium salt | 4.0 | 75 | 90 | 90 | 60 | 60 | 55 | 65 | 50 |

METHODS OF APPLICATION

Whether used as plant growth regulators or as herbicides, the compounds of the present invention are most useful when applied directly to the plants subsequent to their emergence from the soil. In use at an agricultural field site, the compounds are generally embodied in suitable formulations containing additional ingredients and diluent carriers to aid in their dispersal. Examples of such ingredients or carriers are water, organic solvents, dusts, granules, surface active agents, water-in-oil and oil-in-water emulsions, wetting agents, dispersing agents, and emulsifiers. The formulations generally take the form of dusts, solutions, emulsifiable concentrates, or wettable powders.

A. DUSTS

Dusts are dense powder compositions which combine the active compounds with a dense, free-flowing solid carrier. They are intended for application in dry form and are designed to settle rapidly to avoid being windborne to areas where their presence is not desired.

The carrier may be of mineral or vegetable origin, and is preferably an organic or inorganic powder of high bulk density, low surface area, and low liquid absorptivity. Suitable carriers include micaceous talcs, pyrophyllite, dense kaolin clays, tobacco dust, and ground calcium phosphate rock.

The performance of a dust is sometimes aided by the inclusion of a liquid or solid wetting agent, of ionic, anionic, or nonionic character. Preferred wetting agents include alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Dispersants are also useful in the same dust compositions. Typical dispersants include methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N-(long chain acid) taurates.

In addition, inert absorptive grinding aids are frequently included in dust compositions to aid in the manufacturing of the dust. Suitable grinding aids include attapulgite clay, diatomaceous silica, synthetic fine silica and synthetic calcium and magnesium silicates.

In typical dust compositions, carriers are usually present in concentrations of from about 30 to 90 weight percent of the total composition. The grinding aid usually constitutes about 5 to 50 weight percent, and the wetting agent up to about 1.0 weight percent. Dispersants, when present, constitute up to about 0.5 weight percent, and minor amounts of anticaking and antistatic agents may also be present. The particle size of the entire composition is usually about 30 to 50 microns.

B. SOLUTIONS

Aqueous solutions of the active compounds are prepared such that application at the rate of about 1 to about 200 gallons of solution per acre (about 9 to about 1875 liters per hectare) will provide the required amount of active ingredient. A small amount of nonphytotoxic surfactant typically between 0.05% and 0.5% by weight is usually included to improve the wetting ability of the solution and thus its distribution over the plant surface. Anionic, cationic, nonionic, ampholytic, and zwitterionic surfactants are all useful in this regard.

Suitable anionic surfactants include alkali metal, ammonium, and amine salts of fatty alcohol sulfates having from 8-8 carbon atoms in the fatty chain and sodium salts of alkyl benzene sulfonates having from 9 to 15 carbon atoms in the alkyl chain. Suitable cationic surfactants include dimethyl dialkyl quaternary ammonium halides with alkyl chains of 8 to 18 carbon atoms. Suitable nonionic surfactants include polyoxyethylene adducts of fatty alcohols having 10 to 18 carbon atoms, polyethylene oxide condensates of alkyl phenols with alkyl chains of 6 to 12 carbon atoms and 5 to 25 moles of ethylene oxide condensed onto each mole of alkyl phenol, and polyethylene oxide condensates of sorbitan esters with 10 to 40 moles of ethylene oxide condensed onto each mole of sorbitan ester. Suitable ampholytic surfactants include secondary and tertiary aliphatic amine derivatives with one aliphatic substituent containing 8 to 18 carbon atoms and another containing an anionic water-solubilizing group such as a sulfate or sulfonate. Sodium-3-dodecylaminopropionate and sodium-3-dodecyl amino propane sulfonate are examples. Suitable zwitterionic surfactants include derivatives of aliphatic quaternary ammonium compounds with one aliphatic substituent containing 8 to 18 carbon atoms and another containing an anionic water-solubilizing group. Examples of are 3-(N,N-dimethyl-N-hexadecylammonio)propane-1-sulfonate and 3-(N,N-dimethyl-N-hexadecylammonio)-2-hydroxy propane-1sulfonate.

C. EMULSIFIABLE CONCENTRATES

Emulsifiable concentrates are solutions in which the active materials and an emulsifying agent are dissolved in a non-watermiscible solvent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil-soluble petroleum sulfonates, or preferably mixtures of these emulsifying agents. Such emulsifying agents usually comprise about 1 to 10 weight percent of the total composition.

Typical emulsifiable concentrates contain about 15 to 50 weight percent active material, about 40 to 82 weight percent solvent, and about 1 to 10 weight percent emulsifier. Other additives such as spreading agents and stickers can also be included.

D. WETTABLE POWDERS

Wettable powders are water-dispersible compositions containing the active material, an inert solid extender, and one or more surfactants to provide rapid wetting and prevent flocculation when suspended in water.

Suitable solid extenders include both natural minerals and materials derived synthetically from such minerals. Examples include kaolinites, attapulgite clay, montmorillonite clays, synthetic silicas, synthetic magnesium silicate and calcium sulfate dihydrate.

Suitable surfactants include both nonionic and anionic types, and function as wetting agents and dispersants. Usually one of each is included. Preferred wetting agents are alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N(long chain acid) taurates.

Typical wettable powders contain 25 to 90 percent active material, 0.5 to 2.0 percent wetting agent, 0.25 to 5.0 percent dispersant, and from 9.25 to 74.25 weight percent inert extender. Frequently, 0.1 to 1.0 percent of the extender is replaced by a corrosion inhibitor and/or an antifoaming agent.

E. IN GENERAL

In general, any conventional postemergence method of application can be used, including common dusting or spraying equipment. The amount of active ingredient which is effective in producing the desired result, be it herbicidal or growth-regulating, depends on the nature of the plant species to be controlled and the prevailing conditions. Herbicidal effects are usually achieved at 0.1 to 50 pounds active ingredient per acre, preferably 1 to 10, while plant growth regulation is usually achieved at 0.1 to 20 pounds active ingredient per acre, preferably 0.5 to 5. It will be readily apparent to one skilled in the art that compounds of lower activity will require a higher dosage than more active compounds for the same degree of control.

What is claimed is:

1. A compound having the formula $$\begin{array}{c} R_3 \\ | \\ R_2-S(O)_n^{\oplus\ominus} \; O \quad O \\ | \quad\quad\quad \backslash \| \\ R_1 \quad\quad\quad\quad P-CH_2NHCH_2\overset{O}{\overset{\|}{C}}OH \\ / \\ HO \end{array}$$

wherein $R_1$, $R_2$, and $R_3$ represent $C_1$–$C_6$ alkyl, and n is zero or one, wherein no more than two of $R_1$, $R_2$ or $R_3$ are identical.

2. The compound according to claim 1 in which n is zero.

3. The compound according to claim 2 in which $R_1$, $R_2$ and $R_3$ each represent $C_1$–$C_4$ alkyl.

4. The compound according to claim 2 in which $R_1$ and $R_2$ are each n-butyl and $R_3$ is methyl.

5. The compound according to claim 2 in which $R_1$ and $R_2$ are each ethyl and $R_3$ is methyl.

6. The compound according to claim 2 in which $R_1$ and $R_2$ are each methyl and $R_3$ is isopropyl.

7. The compound according to claim 2 in which $R_1$ and $R_2$ are each methyl and $R_3$ is n-butyl.

8. An herbicidal composition comprising an herbicidally effective amount of a compound having the formula $$\begin{array}{c} R_3 \\ | \\ R_2-S(O)_n^{\oplus\ominus} \; O \quad O \\ | \quad\quad\quad \backslash \| \\ R_1 \quad\quad\quad\quad P-CH_2NHCH_2\overset{O}{\overset{\|}{C}}OH \\ / \\ HO \end{array}$$

where $R_1$, $R_2$, and $R_3$ represent $C_1$–$C_6$ alkyl, and n is zero or one, wherein no more than two of $R_1$, $R_2$ or $R_3$ are identical, and an inert diluent carrier.

9. An herbicidal composition according to claim 8 in which n is zero.

10. An herbicidal composition according to claim 9 in which $R_1$, $R_2$ and $R_3$ each represent $C_1$–$C_4$ alkyl.

11. An herbicidal composition according to claim 9 in which $R_1$ and $R_2$ are each n-butyl and $R_3$ is methyl.

12. An herbicidal composition according to claim 9 in which $R_1$ and $R_2$ are each ethyl and $R_3$ is methyl.

13. An herbicidal composition according to claim 9 in which $R_1$ and $R_2$ are each methyl and $R_3$ is isopropyl.

14. An herbicidal composition according to claim 9 in which $R_1$ and $R_2$ are each methyl and $R_3$ is n-butyl.

15. A method of controlling undesirable vegetation comprising applying to the vegetative in post-emergent state an herbicidal composition comprising an herbicidally effective amount of a compound having the formula $$\begin{array}{c} R_3 \\ | \\ R_2-S(O)_n^{\oplus\ominus} \; O \quad O \\ | \quad\quad\quad \backslash \| \\ R_1 \quad\quad\quad\quad P-CH_2NHCH_2\overset{O}{\overset{\|}{C}}OH \\ / \\ HO \end{array}$$

where $R_1$, $R_2$, and $R_3$ represent $C_1$–$C_6$ alkyl, and n is zero or one, wherein no more than two of $R_1$, $R_2$ or $R_3$ are identical, and an inert diluent carrier.

16. The method according to claim 15 in which n is zero.

17. The method according to claim 16 in which $R_1$, $R_2$ and $R_3$ each represent $C_1$–$C_4$ alkyl.

18. The method according to claim 16 in which $R_1$ and $R_2$ are each n-butyl and $R_3$ is methyl.

19. The method according to claim 16 in which $R_1$ and $R_2$ are each ethyl and $R_3$ is methyl.

20. The method according to claim 16 in which $R_1$ and $R_2$ are each methyl and $R_3$ is isopropyl.

21. The method according to claim 16 in which $R_1$ and $R_2$ are each methyl and $R_3$ is n-butyl.

22. A method of controlling undesirable vegetation in the post-emergent state by applying to the vegetation a post-emergent herbicidally effective amount of a tri-mixed alkylsulfonium salt of N-phosphonomethylglycine wherein said alkyl groups each contain from 1 to 6 carbon atoms and wherein no more than two of said alkyl groups are identical.

23. The method of claim 22 wherein said alkyl groups each contain 1 to 4 carbon atoms and no more than two of said alkyl groups are identical.

24. A method of controlling undesirable vegetation in the post-emergent state by applying to the vegetation a post-emergence herbicidally effective amount of a tri-mixed alkylsulfoxonium salt of N-phosphonomethylglycine wherein said alkyl groups each contain from 1 to 6 carbon atoms and wherein no more than two of said alkyl groups are identical.

25. The method of claim 24 wherein said alkyl groups each contain 1 to 4 carbon atoms and no more than two of said alkyl groups are identical.

26. An herbicidal composition comprising a post-emergent herbicidally effective amount of a tri-mixed alkylsulfonium salt of N-phosphonomethylglycine wherein said alkyl groups each contain from 1 to 6 carbon atoms and wherein no more than two of said alkyl groups are identical, and an inert diluent carrier.

27. The method of claim 26 wherein said alkyl groups each contain 1 to 4 carbon atoms and no more than two of said alkyl groups are identical.

28. An herbicidal composition comprising a post-emergence herbicidally effective amount of a tri-mixed alkylsulfoxonium salt of N-phosphonomethylglycine wherein said alkyl groups each contain from 1 to 6 carbon atoms and wherein no more than two of said alkyl groups are identical, and an inert diluent carrier.

29. The method of claim 28 wherein said alkyl groups each contain 1 to 4 carbon atoms and no more than two of said alkyl groups are identical.

30. Compounds corresponding to tri-mixed alkylsulfonium salts of N-phosphonomethylglycine according to claim 1 wherein said alkyl groups each contain from 1 to 6 carbon atoms and wherein no more than two of said alkyl groups are identical.

31. Compounds of claim 30 wherein said alkyl groups each contain 1 to 4 carbon atoms and no more than two of said alkyl groups are identical.

32. Compounds corresponding to tri-mixed alkylsulfoxonium salts of N-phosphonomethylglycine according to claim 1 wherein said alkyl groups each contain from 1 to 6 carbon atoms and wherein no more than two of said alkyl groups are identical.

33. Compounds of claim 32 wherein said alkyl groups each contain 1 to 4 carbon atoms and no more than two of said alkyl groups are identical.

* * * * *